US007951300B2

(12) United States Patent
Bhandari et al.

(10) Patent No.: US 7,951,300 B2
(45) Date of Patent: May 31, 2011

(54) WATER-SCALE NEEDLE ARRAY (75) Inventors: Rajmohan Bhandari, Salt Lake City, UT (US); Sandeep Negi, Salt Lake City, UT (US); Florian Solzbacher, Salt Lake City, UT (US); Richard A. Normann, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 861 days.

(21) Appl. No.: 11/807,764

(22) Filed: May 29, 2007

(65) Prior Publication Data

US 2008/0138582 A1 Jun. 12, 2008

Related U.S. Application Data (60) Provisional application No. 60/831,557, filed on Jul. 17, 2006.

(51) Int. Cl.
*C25F 3/00* (2006.01)
*B44C 1/22* (2006.01)
(52) U.S. Cl. .............. 216/11; 216/39; 216/52; 216/91; 216/99; 438/460; 438/691
(58) Field of Classification Search ............. 216/11, 216/39, 52, 91, 99; 438/128, 460, 690, 692, 438/691
See application file for complete search history.

(56) References Cited

U.S. PATENT DOCUMENTS

| 5,215,088 | A | 6/1993 | Normann et al. |
| 5,472,592 | A | 12/1995 | Lowery |
| 5,689,603 | A | 11/1997 | Huth |
| 5,895,562 | A | 4/1999 | Dubin |
| 6,285,446 | B1 | 9/2001 | Farhadiroushan |
| 6,896,850 | B2 * | 5/2005 | Subramanian et al. ....... 422/102 |

OTHER PUBLICATIONS

Fofonoff, T. et al. Assembly-ready brain microelectrode array's in: Engineering in Medicine and Biology Society, Proceedings of the 25th Annual International Conference of the IEEE, 2003, pp. 1937-1940.
Fofonoff, T. et al. A highly flexible manufacturing technique for microelectrode array fabrication in: [Engineering in Medicine and Biology, 2002. 24th Annual Conference and the Annual Fall Meeting of the Biomedical Engineering Society] EMBS/BMES Conference, 2002, pp. 2107-2108.
Campbell, Patrick et al. "A silicon-based, three-dimensional neural interface: manufacturing processes for an intracortical electrode array," IEEE, Aug. 1991, pp. 758-768, vol. 38.No. 8.
Jones, Kelly et al. "A glass/silicon composite intracortical electrode array,"Annals of Biomedical Engineering, 1992, pp. 423-437, vol. 20.

* cited by examiner

*Primary Examiner* — Donald Loney
(74) *Attorney, Agent, or Firm* — Thorpe North & Western LLP (57) ABSTRACT Methods for wafer-scale fabrication of needle arrays can include mechanically modifying a wafer to produce a plurality of vertically-extending columns. The columns are etched to round and reshape the columns into substantially uniformly shaped needles. Needle arrays having needle width non-uniformity of less than about 3% and length non-uniformity of less than about 2% can be produced.

7 Claims, 5 Drawing Sheets

WATER-SCALE NEEDLE ARRAY

RELATED APPLICATIONS

This application claims the benefit of and hereby incorporates by reference U.S. Provisional Patent Application Ser. No. 60/831,557, filed Jul. 17, 2006, and entitled "An Integrated Wireless Neural Interface for Chronic Recording and Stimulation."

This application is also related to U.S. patent application Ser. No. 11/807,763, entitled "MASKING HIGH ASPECT-RATIO STRUCTURES", and U.S. patent application Ser. No. 11/807,766, entitled "MICRO-NEEDLE ARRAYS HAVING NON-PLANAR TIPS AND METHODS OF MANUFACTURE THEREOF", each of which is filed concurrently herewith and are hereby incorporated by reference.

GOVERNMENT RIGHTS

This invention was made with government support by the National Institutes of Health under Contract No. HHSN265200423621C and the Defense Advanced Research Projects Agency under Award No. 908164. The government has certain rights to this invention.

BACKGROUND

1. Field of the Invention

The present invention relates generally to needle array devices and methods of fabrication.

2. Related Art

The potential for implanting electronic devices into patients with direct interface to the neural system is vast. Systems which may enable paraplegics to regain control of their bladder or limbs, provide vision for the blind, or restore vocal cord function are all under development, and promising initial results have been obtained in some experiments.

A key component of some implantable systems is a needle array to enable interfacing of the electronics with a neuron or directly into brain tissue. For example, U.S. Pat. No. 5,215,088 to Normann et al. discloses a three-dimensional electrode device which can be used as a neural or cortical implant. The device of Norman, also known as the Utah Electrode Array (UEA), can be used to provide a neural interface to electronic equipment for sensing and/or stimulation. Alternative approaches for fabricating similar devices are known, but require a large number of masking steps which also slows down production and increases cost of manufacture.

While the UEA has been in experimental use for a number of years, fabrication techniques have been relatively unrefined. Fortunately, demand for the UEA has been limited to experimental use, so few devices are needed. With greater experimental usage, and the eventual possibility for production level requirements, existing fabrication techniques may provide inadequate quality, repeatability, and throughput.

SUMMARY

Briefly, and in general terms, the invention is directed to techniques for wafer-scale fabrication of needle arrays. In one embodiment, the invention includes a method for wafer-scale fabrication of needle arrays. The method may include mechanically modifying a provided wafer to produce a plurality of vertically-extending columns. The vertically-extending columns are etched under conditions suitable to produce a plurality of substantially uniformly shaped needles from the plurality of vertically-extending columns. After etching, the wafer can be separated into a plurality of individual needle arrays. Needle arrays manufactured by this method can provide improved uniformity of the needle geometry (e.g. width and length).

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIGS. 6($a$) and 6($b$) are a top view and side view, respectively, of a holder for holding a wafer when being etching in accordance with an embodiment of the present invention.

Figure 1:
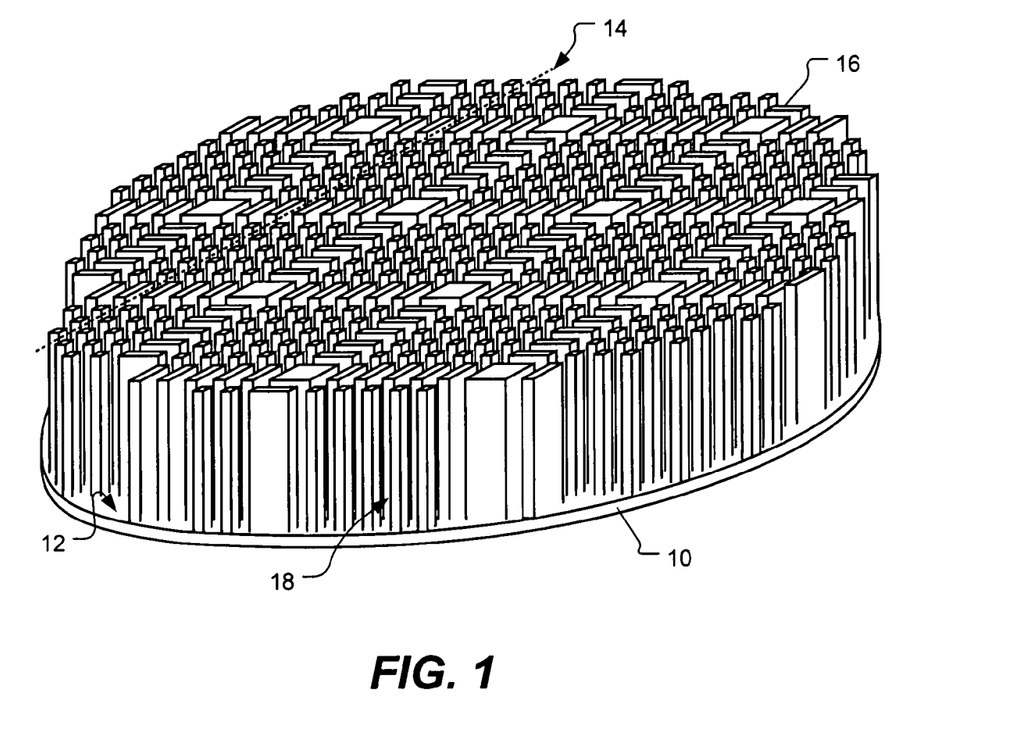
FIG. 1 is a perspective illustration of a wafer that has been mechanically modified to produce a plurality of vertically extending columns in accordance with an embodiment of the present invention.

It will be understood that these figures are provided merely for convenience in describing the invention and are drawn for purposes of clarity rather than scale (other than the micrographs). As such, actual dimensions may, and likely will, deviate from those illustrated in terms of relative dimensions, contours, and the like. For example, FIG. 1 illustrates an embodiment showing about nine array areas where actual wafers would likely include dozens to hundreds of arrays per wafer.

DETAILED DESCRIPTION OF EXAMPLE EMBODIMENT(S)

In describing embodiments of the present invention, the following terminology will be used.

The singular forms "a," "an," and "the" include plural referents unless the context clearly dictates otherwise. Thus, for example, reference to "a needle" includes reference to one or more of such needles and "etching" includes one or more of such steps.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "50-250 micrometers should be interpreted to include not only the explicitly recited values of about 50 micrometers and 250 micrometers, but also include individual values and sub-ranges within the indicated range. Thus, included in this numerical range are individual values such as 60, 70, and 80 micrometers, and sub-ranges such as from 50-100 micrometers, from 100-200, and from 100-250 micrometers, etc. This same principle applies to ranges reciting only one numerical value and should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall expressly include "exactly," consistent with the discussion above regarding ranges and numerical data.

As mentioned above, needle arrays, such as the Utah Electrode Array (UEA) have been the subject of experimental use. Because production of UEAs has been limited to date, there has been little need investigate means for mass producing the UEA device. Accordingly, fabrication of the UEA to date has been one array at a time. This process is time consuming, and has yielded less consistency in results that desired.

An improved method of fabricating needle arrays, such as the UEA, has been developed which can be performed on a wafer-scale. Benefits of the improved method include fast throughput and more consistent needle shape in the finished products.

In an embodiment, the method includes providing a wafer from which the needle array is to be constructed. The wafer can be, for example, a mono-crystalline silicon wafer. Mono-crystalline silicon wafers are typically cut from a single crystal silicon ingot, for example as for integrated circuit manufacturing. It will be appreciated that the silicon wafer need not be perfectly single crystal, as most semiconductor grade silicon wafers contain a small number of defects of various types. Other wafer materials that can be used include ceramic material, polymers, or any other material having sufficient mechanical strength and capacity to form array features on the scale discussed.

The method further includes mechanically modifying the wafer to produce a plurality of vertically extending columns, for example as illustrated in FIG. 1. Mechanical modification of the wafer can be accomplished using any suitable technique such as, but not limited to, sawing, ablation, or any other suitable material removal technique. For example, mechanically modifying the wafer can be performed by sawing the wafer 10 on a front side 12 along a first plurality of lines 14 to produce a plurality of vertically-extending columns 16. The sawing can produce saw kerfs 18 which extend into the wafer. For example, the wafer may be about 2 mm thick, and the saw kerfs extend about 1.5 mm into the wafer although other dimensions can also be readily produced. The wafer can be sawed or cut using a dicing saw. Alternate techniques for cutting the trenches may include deep reactive ion etching.

As can be seen in FIG. 1, depending on the spacing of the saw cuts, the size of the columns produced can be varied. By forming evenly spaced saw cuts in one direction, and then turning the wafer 90 degrees with respect to the cutting path and making a second set of evenly spaced saw cuts, a plurality of square columns can be produced. For example, the columns can be about 250 micrometers on each side, spaced about 400 micrometers apart. Spacing can be varied to produce rectangular columns and different size square columns. Similarly, spacing can be varied to achieve open areas between arrays and/or provide for other non-array type features, e.g. contacts, supports, insertion stops, etc. Further, in some embodiments of the present invention, more than one set of saw cuts can be used. For example, three sets of saw cuts at 60 degrees relative to each other can be performed to form triangular- or hexagonal-shaped columns.

The method of the present invention also includes etching the wafer to reshape the vertically-extending columns under conditions suitable to produce a plurality of substantially uniformly shaped needles from the vertically-extending columns. For example, etching can be performed using a dynamic etch to round the columns and a static etch to form points at the tips of the columns. Suitable etching solutions can include, but are not limited to, mixtures of hydrofluoric acid and nitric acid, TMAH, or any other etchant suitable for controlled etching of the material forming the columns.

Dynamic etching can be performed by placing the wafer into a holder and immersing the wafer in an etching solution. The holder can be constructed of a material which is resistant to the etching solution, such as polytetrafluoroethylene (e.g. Teflon®) or other polymers. The holder can include a gasket to help prevent contact between the back side of the wafer and the etching solution. The immersed wafer is rotated in one direction, while a stirrer stirs the etching solution in an opposite direction to provide aggressive and continuous flow of fresh etching solution into the dicing kerfs.

Figure 6A:
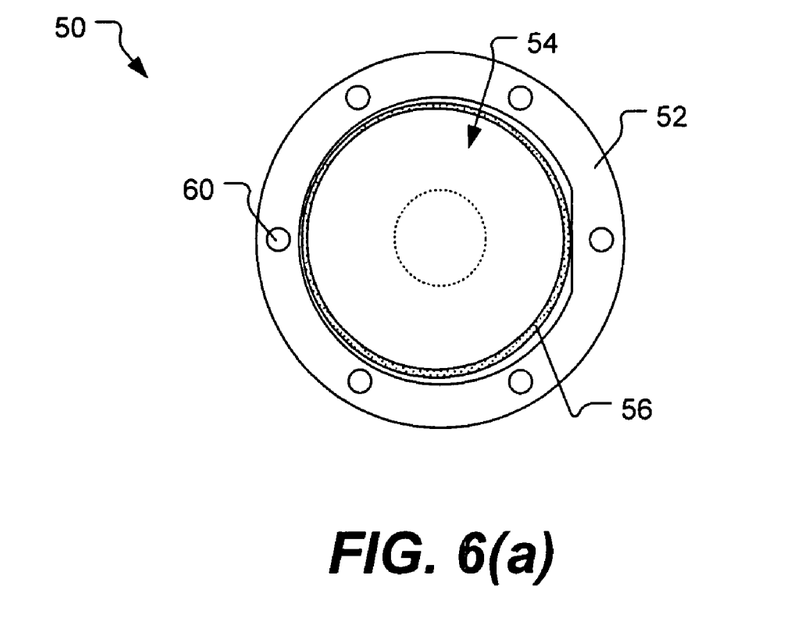
Figure 6B:
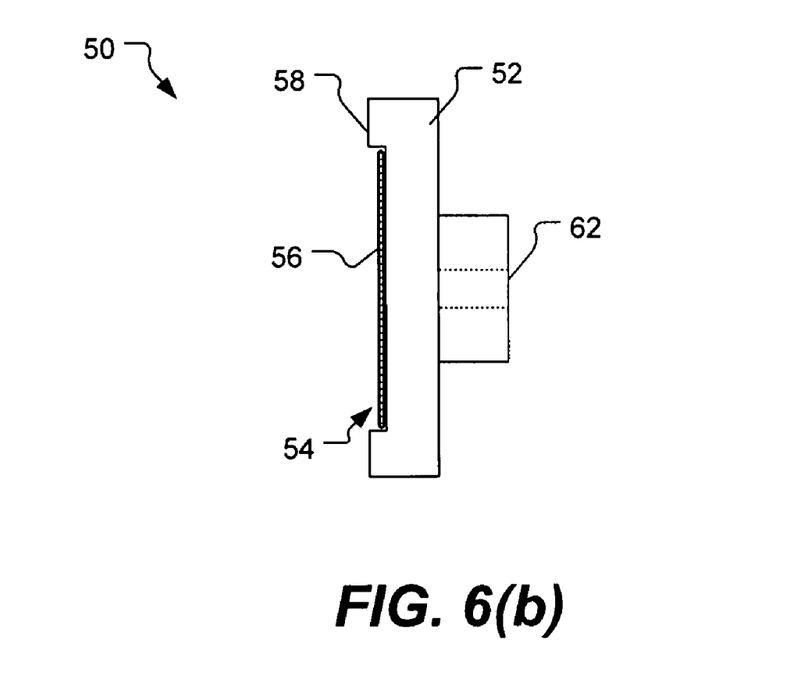

For example, as shown in FIG. 6(a) and FIG. 6(b), an exemplary holder 50 for the wafer can include a main body 52 with a recess 54 to receive the wafer. An O-ring 56 can protect the backside of the wafer from the etchant and a hollow lid (not shown) can be affixed to the front side 58 to cover and hold the wafer in place. The lid can be attached to the holder with the help of six screws received into screw holes 60 in the main body. The back of the holder can include various attachment structures, such as a threaded hole 62 to allow the holder to be fixed into the etching apparatus.

Time duration and rotation rates to provide uniform etching were determined experimentally. For a 3 inch wafer, having columns of 250 micrometers on a side, dynamic etching was performed in an etching solution of 5% hydrofluoric (49% conc) and 95% nitric acid (69% conc). A 7.5 inch diameter basis and a 3 inch long stirring bar were used. The rate of etching is approximately linear with time. Etching is faster at the convex corners of the columns, helping to round the shape of the columns. Accordingly, an etching time of about 4 minutes reduces the square columns to rounded column. Rotation rates of the wafer holder and the stirrer bar can affect the uniformity of the etched columns. For the conditions described above, the wafer holder can be rotated clockwise at about 22 revolutions per minute (rpm) while the stirrer bar is counter rotated at about 500 rpm to provide needle width uniformity of about 2% as described further below. Spacing between the wafer and the stirrer can be about two inches, although a range of about 1.5 to 2 inches, or more particularly, about 1 to 3 inches appears to provide consistent results. The total volume of acid used to etch a 3-inch wafer during dynamic etching was 1494 ml while for static etching it was 747 ml. These parameters can be adjusted and optimized for a particular configuration of columns and materials.

The static etching can be performed by inverting the holder to position the wafer columns in an upward direction and placing the wafer into etchant solution which is not stirred. In the static etching, the etching at the tips of the columns is faster than near the bases, because little fluid motion is present to replenish etching solution near to bottoms of the kerfs. This preferentially shapes the columns into needles. Using the same etching solution as described above, static etching can be performed for about 8 minutes although other times may also be suitable. By varying the dynamic and/or static etching time, the geometry of electrode can be varied. The shapes can range from cylindrical, to pen shape, to conical.

Additional processing steps can be performed to deposit electrically conductive material onto the needles to provide a low impedance electrical connection from the tissue in which the needle array is inserted to the needle body. The coating may be, for example, one or more metals, designed to adhere to the needle body and provide an Ohmic contact between the metal and the needle body. The coating helps to provide a stable interface when inserted in vivo. For example, for silicon micro-needles, a metal stack of iridium over platinum over titanium has found to provide good performance. For example, about 50 nanometers of titanium, following by about 240 nanometers of platinum, followed by about 100 nanometers of iridium were deposited by sputtering. The titanium provides an adhesion layer to the silicon needle body, the platinum provides a diffusion barrier, and the iridium when converted to iridium oxide provides a stable low-impedance electric interface when inserted in vivo. Iridium can be converted to iridium oxide by electrochemical activation. Electrical contacts can also be placed in the back side of the needle array.

Other coating can be used, including for example combinations of titanium and iridium, platinum and iridium, or even direct sputtering in oxygen plasma of iridium oxide directly onto the silicon needle tips.

The micro-needle array may be encapsulated in a non-conductive, non-reactive material to help improve compatibility in vivo. For example, materials can include parylene-C, silicon carbide, and/or silicone. Parylene-C can, for example, be deposited by low-pressure chemical vapor deposition. It will be appreciated that the tips can be left unencapsulated to allow electric contact between the micro-needles and the tissue into which the array is inserted. For example, the tips may be masked prior to the encapsulation. Alternately, the entire needles may be encapsulated, and then the non-conductive, non-reactive material removed from the tip portions.

Various ways of removing the encapsulation from the tips can be used. For example, reactive ion etching using inductively coupled oxygen plasma can be performed. Masking of the lower portion of the needles can be provided by filling the electrode array with photo resist until all electrodes are submerged in the photo resist. After curing the photo resist, the plasma etching removes the photo resist starting from the tips, and as the parylene coated electrodes are exposed, the parylene is also etched away.

Alternately, masking can be performed as described in concurrently filed, commonly-owned and co-pending U.S. patent application Ser. No. 11/807,763, entitled "MASKING HIGH ASPECT-RATIO STRUCTURES".

As yet another example, the tips of the needles may be de-encapsulated using laser ablation (e.g., using an excimer laser) and shadow masking techniques. For example, a shadow mask can be made by forming holes in a wafer in positions corresponding to the needles. The holes may be etched, for example using an anisotropic etchant (e.g. KOH or TMAH) or by deep reactive ion etching. The array can then be temporarily joined to the shadow mask and the needles can be inserted through the holes. The thickness of the shadow mask is equal to the height of the electrodes minus the desired exposure height of de-incapsulation.

It can also be helpful to electrically insulate the needles from each other. This can be accomplished by cutting a third set of trenches into a back surface of the wafer. These cuts define a series of mesas on the back side (called mesas, since they are typically much shorter than the front-side columns). The trenches between the mesas are filled with an electrically insulating material. This operation can be optionally performed before cutting the first set and the second set of trenches into the top side of the wafer. The first set and the second set of trenches can be cut sufficiently deeply into the top side of the wafer to intersect the third set of trenches (reaching the insulating material), thus removing all of the original wafer material between the columns that will be formed into the micro-needles. The insulating material can be, for example, glass. A glass frit can be disposed into the third set of trenches and then heating to melt and anneal the glass. Glass frit can be dispensed in the trenches using screen printing technique for high production manufacture of arrays. Although glass frit is mentioned, other insulating materials can be used which are biocompatible, non-toxic, and can be reliably deposited in the trenches. Thus, in these embodiments, the insulating material forms a support matrix for the micro-needles which are segregated from one another.

As another example, a polymer can be patterned into the trenches (e.g. using standard lithographic techniques) or reflowed into the trenches. For example, the polymer may be a biocompatible polymer, such as benzocyclobutane. As another example, the polymer may be biodegradable polymer, such as but not limited to, polycaprolactone (PCL), poly (DL-lactide-co-glycolide) or polyglycolide. Any polymer which biodegrades, is non-toxic, and does not interfere with performance of the micro-needles can be used. The polymer helps to support the micro-needles during implantation. After implantation, the biodegradable plastic will dissolve, allowing the micro-needles to float in the tissue. This reduces mechanical coupling between the array and the tissue, helping to reduce neural damage and possible fracturing of the needles.

Following the steps of cutting and etching the columns to form the needles, the material flowed into the third set of trenches will form the substrate of the needle array. Of course, if these steps are not performed, the substrate of the needle array will be the base wafer material.

When wafer-scale fabrication steps are completed, the wafer can be separated into a plurality of individual needle arrays such as by conventional dicing or other techniques. Additional fabrication steps may be performed on the individual needle arrays, such as flip chip mounting of an integrated circuit to the needle array. Optionally, these additional fabrication steps can be performed while the arrays are still associated on the wafer. In this manner, at least some of the fabrication steps can be streamlined and performed simultaneously across the wafer. In most cases, this may involve performing various deposition and/or photolithographic steps to the backside of the wafer and care should be taken to protect the micro-needles.

Figure 3:
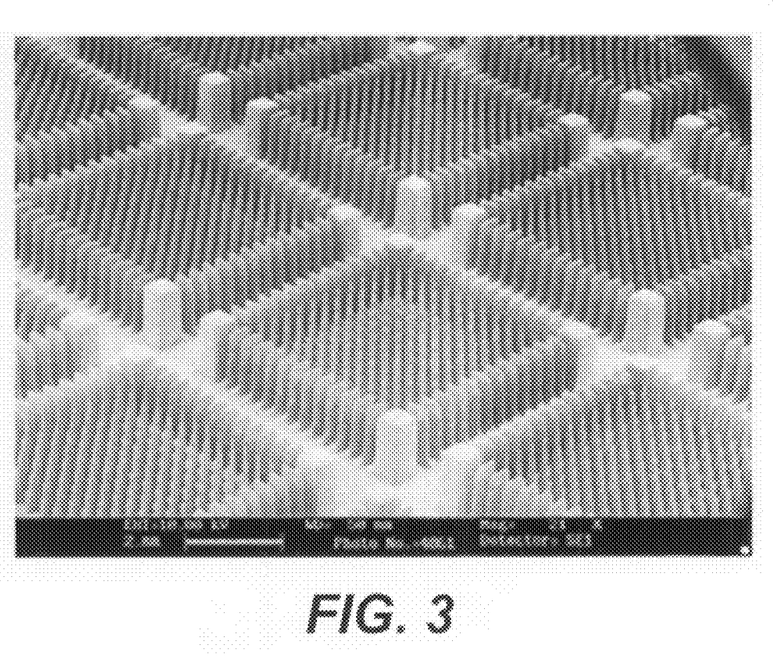
FIG. 3 is a scanning electron microscope picture of a three-inch wafer of etched needle arrays in accordance with an embodiment of the present invention.

To provide greater uniformity in the finished width of the needles, a plurality of sacrificial columns can be defined when mechanically modifying the wafer. For example, typically individual needle arrays have a gap left in between to simplify separation of the individual needle arrays once wafer-scale fabrication is completed. The gap can allow increased flow of etchant near the outside edges of the arrays during the dynamic etching, causing the outside needles to be etched faster than the inside needles. Accordingly, sacrificial features can be included to help provide more uniform etchant flow through the saw kerfs. For example, sacrificial features can include extra rows and columns of needles that are removed during a later processing step. As another example, differently sized columns in the form of rectangular fins or square posts can be included near the gaps to provide a relatively constant column sidewall area density across the wafer. In other words, where wider cuts are present, larger columns can be included near the wide cuts to help counteract the increased flow in that vicinity. The sacrificial columns can be removed after the etching using a dicing saw. Non-limiting examples of such sacrificial features are shown in FIG. 1 as larger square columns and rectangular columns forming a grid outlining individual arrays. Similarly, FIG. 3 is an SEM picture of sacrificial columns around the periphery of individual arrays on an actual wafer having a plurality of arrays formed thereon.

It has been unexpectedly found that relatively uniform needle shapes can be obtained by performing the etching on a wafer scale. For example, width uniformity has been experimentally measured for the wafer-scale fabrication methods disclosed herein. After sawing, the column widths were 225+/−15 micrometers measured over five wafers. This variability is primarily due to wearing of the dicing blade. All five wafers were etched under a dynamic etching process for 4 minutes under similar conditions. The etch rate was approximately 25 micrometers/minute at room temperature. Measurements of needle width in two-directions (both horizontal relative to the wafer top surface) were performed diagonally across the rounded columns of fifteen individual arrays distributed across each of the wafers. The average width was 122+/−7 micrometers. The percentage variation in non-uniformity of electrode measurements was calculated as the standard deviation multiplied by 100 and divided by the mean. The average percentage of width non-uniformity across all wafers was about 2%, while within an individual array it was about 1.5%. Accordingly, the process can consistently produce needles with non-uniformity of less than about 3%.

After static etching, all five wafers were cross-sected using a dicing saw and needle lengths were measured across each array. Seven arrays on each wafer were analyzed. The average needle length was 1.3 mm and the percentage of length non-uniformity was found to be about 1%. Accordingly, the process can consistently produce needles with a length non-uniformity of less than about 2%.

Data was also collected for the previous single array etching process by etching ten arrays. Width measurements were made diagonally across each array. Width non-uniformity was found to be about 9% in one direction and about 10% in the other direction. Accordingly the wafer-scale etching process provides a significant improvement in the width uniformity of the needles, improving width non-uniformity from about 9-10% in the single array process to less than 5%, and more particularly, less than 3% in the wafer-scale etching process and improving length non-uniformity to less than 5%, and more particularly less than 2% in the wafer-scale etching process.

Performing wafer level etching can significantly reduce the processing time. For example, using wafer-scale etching, a single 3-inch wafer can be etched in about 13 minutes to produce 54 UEAs. In contrast, conventional single array etching would require about 27 hours to produce the same number of arrays. Although dimensions of UEAs can vary, the number of UEAs which can be formed from a single 3-inch wafer can typically range from about 40 to about 80, while larger wafers can be effectively used to produce up to several hundred UEAs per wafer. Further, UEA dimensions can range from about 1 mm to about 10 mm across, although other dimensions can be readily formed depending on the intended application.

Figure 2:
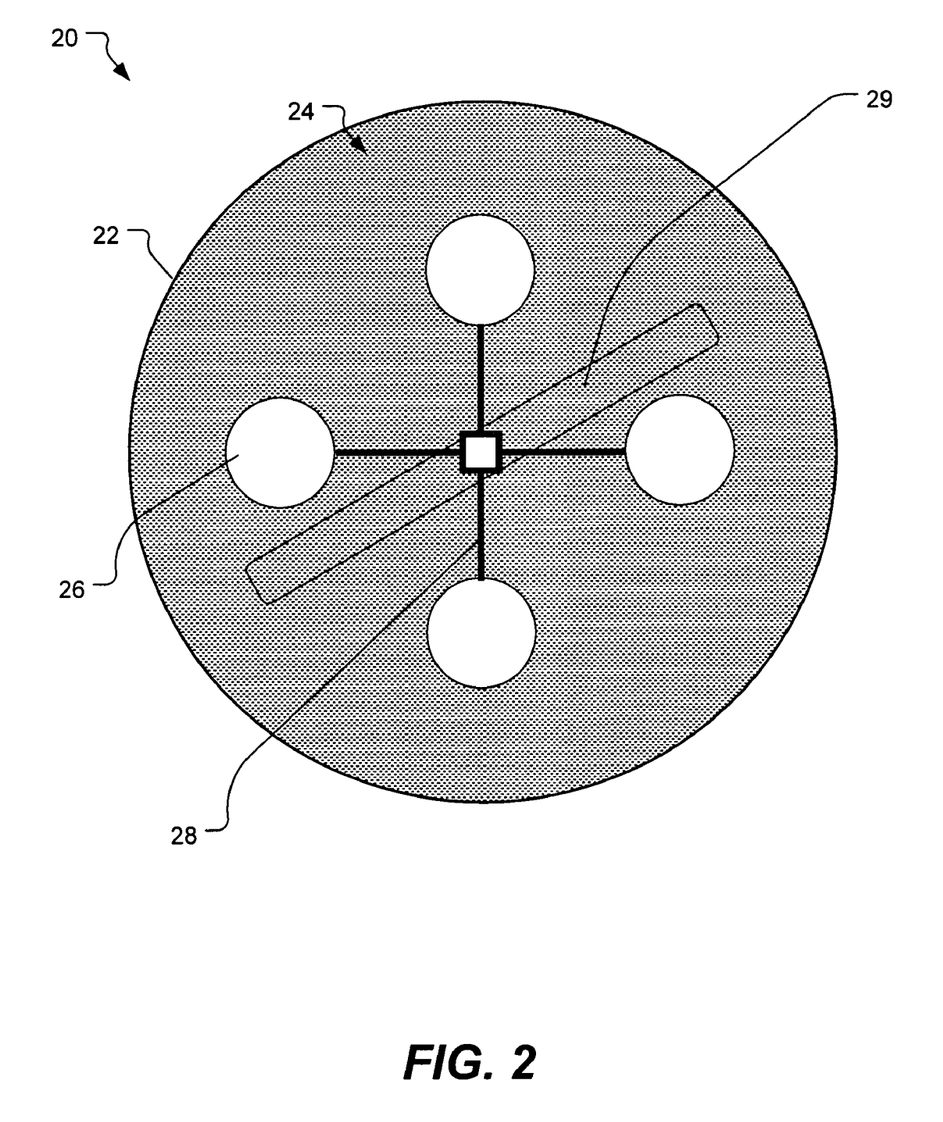
FIG. 2 is a schematic illustration of a system for etching multiple-wafers simultaneously in accordance with an embodiment of the present invention.

For faster throughput in the etching process, a larger etching bath may be used and multiple wafers etched simultaneously. For example, FIG. 2 illustrates a schematic of a multiple-wafer etching system 20. The system includes a vessel 22 to hold liquid etchant 24 into which a plurality of wafers 26 are immersed while held by a holder 28. The holder can rotate. A stirrer bar 29 (e.g. a magnetic stirrer bar) stirs the etchant.

Figure 4:
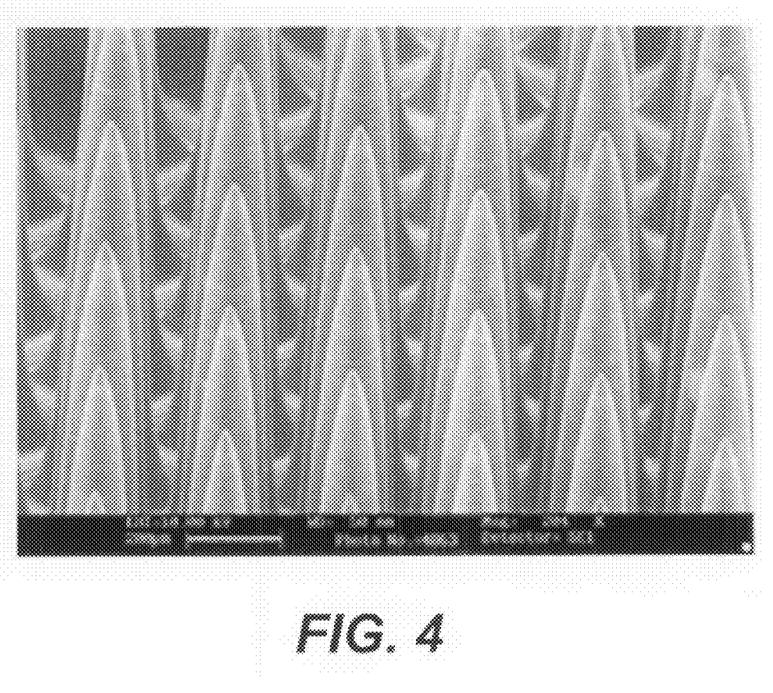
FIG. 4 is an enlarged view of a portion of FIG. 3.

A scanning electron microscope picture of a three-inch wafer of etched needle arrays is shown in FIG. 3. It can be seen that the wafer includes a plurality of needle arrays disposed on the wafer, each of the needle arrays having a plurality of substantially parallel needles. FIG. 4 illustrates a close-up zoom view of FIG. 3 showing rounded columns and tips etched from substantially square columns using a sequential combination of dynamic and static etching steps.

Figure 5:
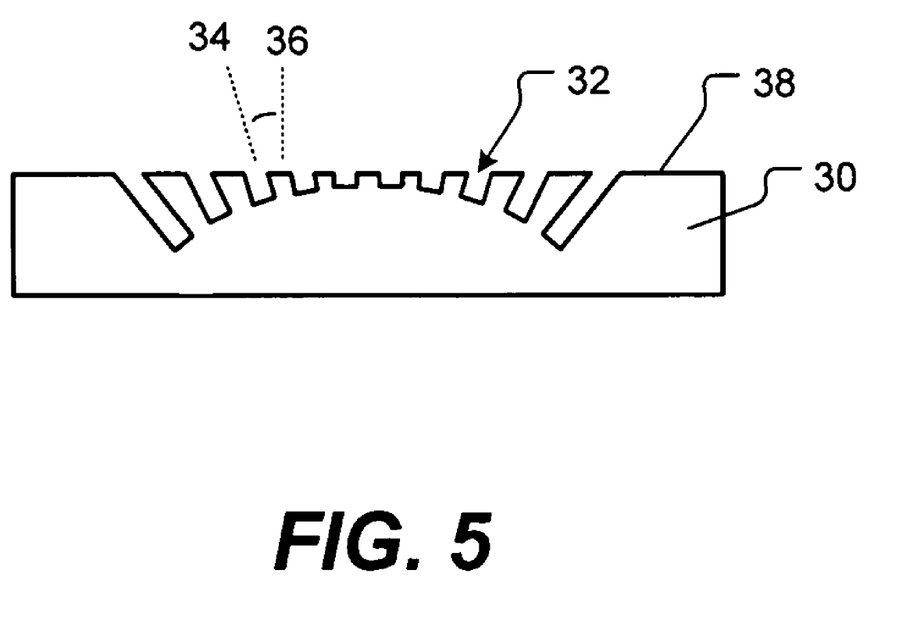
FIG. 5 is a side view illustration of wafer having a plurality of trenches cut at angles and having varying depth from the surface in accordance with an embodiment of the present invention.

A number of variations on the basic needle arrays as described above can be produced. For example, while the discussion above has assumed that the sawing is performed perpendicularly to the surface to produce parallel needles, if desired the saw may be angled to produce arrays of needles which are splayed inward or outward. For example, FIG. 5 provides a side view of a wafer 30 having a plurality of trenches 32 cut at an angle 34 relative to the vertical 36 of the surface 38. Remaining processing steps can occur as described above. Alternatively, or in addition to, the sawing may be angled in parallel slanted kerfs such that all of the columns angle at substantially the same angle with respect to the substrate. Such non-parallel micro-needle arrays can be useful where insertion forces or the intended application would not shear the micro-needles off of the substrate.

The depths of the trenches can also be optionally varied to produce different length needles. If desired, various curved surfaces can be formed, and needle arrays presenting tips and/or bases disposed in a non-planar surface can be formed as described further in co-pending U.S. patent application Ser. No. 11/807,766, entitled "MICRO-NEEDLE ARRAYS HAVING NON-PLANAR TIPS AND METHODS OF MANUFACTURE THEREOF".

Summarizing and reiterating to some extend, a wafer-scale method for making needle arrays has been developed. Benefits of the wafer-scale method include increased throughput, as an entire wafer of needle arrays can be manufactured simultaneously, rather than forming a single needle array at a time. An additional benefit of the wafer-scale method is improved uniformity in the width and length of the needles across an individual array. During etching, a wafer holder can protect the back side of the wafer from etching using an o-ring, avoid the need for organic masking materials, such as wax that could present cleaning difficulties during later processing steps.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

The invention claimed is:
1. A method of wafer-scale fabrication of high-aspect ratio needle arrays comprising:
providing a mono-crystalline silicon wafer;

sawing the wafer on a back side along a first plurality of lines to produce a plurality of mesas;

forming glass between the plurality of mesas;

sawing the wafer on a front side along a second plurality of lines to a depth sufficient to intersect the glass to produce a plurality of vertically-extending columns, the vertically-extending columns arranged into a plurality of individual arrays of columns separated by sacrificial columns;

placing the wafer into a holder so the plurality of vertically-extending columns are exposed and the back side of the wafer is sealed within the holder;

immersing the wafer into an etching solution having a mixture of hydrofluoric acid and nitric acid;

simultaneously stirring the etching solution in one direction with a stirrer while rotating the wafer in an opposite direction for a first time interval to reshape the vertically-extending columns into rounded columns;

positioning the wafer into the etching solution with the vertically-extending columns in an upward position for a second time interval to produce a plurality of substantially uniformly shaped needles from the plurality of rounded columns; and separating the wafer into a plurality of individual needle arrays after etching.

2. The method of claim 1, wherein the first time interval is about 4 minutes and the second time interval is about 8 minutes.

3. The method of claim 1, wherein the uniformly shaped needles have a width non-uniformity of less than about 3% and a length non-uniformity of less than about 2%.

4. The method of claim 1, further comprising depositing electrically conductive material on the uniformly shaped needles.

5. The method of claim 1, further comprising depositing electrically insulative material on the uniformly shaped needles except at tip portions of the needles.

6. The method of claim 1, wherein the uniformly shaped needles have a length non-uniformity of less than about 5%.

7. The method of claim 1, wherein the plurality of substantially uniformly shaped needles include extra rows of sacrificial needles formed from extra rows of sacrificial columns in the plurality of vertically-extending columns.

* * * * *